United States Patent [19]
Angenendt et al.

[11] Patent Number: 6,124,470
[45] Date of Patent: Sep. 26, 2000

[54] METHOD FOR WORKING UP BENZIMIDAZOLONE-CONTAINING REACTION MIXTURES

[75] Inventors: Heinrich Angenendt, Idstein; Bert Willi Portz, Frankfurt; Horst Walter, Hattersheim, all of Germany

[73] Assignee: Clariant GmbH, Frankfurt, Germany

[21] Appl. No.: 08/733,392

[22] Filed: Oct. 18, 1996

[30] Foreign Application Priority Data

Oct. 20, 1995 [DE] Germany .................. 195 39 114

[51] Int. Cl.⁷ .................................................. C07D 235/26
[52] U.S. Cl. ................................................ 548/306.4
[58] Field of Search ........................................ 548/306.4

[56] References Cited

U.S. PATENT DOCUMENTS 4,138,568  2/1979  Hari et al. .................. 548/305

FOREIGN PATENT DOCUMENTS 27 25 957  12/1977  Germany .

*Primary Examiner*—Laura L. Stockton
*Attorney, Agent, or Firm*—Connolly Bove Lodge & Hutz LLP

[57] ABSTRACT

The present invention relates to a process for working up reaction mixtures containing benzimidazolones of the formula (I)

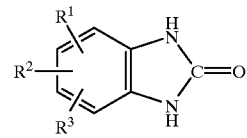

prepared by reacting o-phenylenediamines and urea in a water-insoluble solvent, where in formula (I) $R^1$, $R^2$ and $R^3$ are identical or different and independently of one another are a hydrogen atom, an alkyl, alkoxy or alkylsulfonyl group having in each case 1 to 6 carbon atoms, chlorine, bromine, a substituted or unsubstituted phenyl group, a carboxylic acid, methylcarbonyl, phenylcarbonyl, methoxycarbonyl, carbamoyl, methylcarbamoyl or phenylcarbamoyl group, a hydroxyl group, cyano group or nitro group, by adding a wetting agent and a defoamer to the reaction mixture, distilling off the solvent azeotropically with the addition of water and with stirring and filtering off the benzimidazolone from the aqueous suspension arising.

20 Claims, No Drawings

METHOD FOR WORKING UP BENZIMIDAZOLONE-CONTAINING REACTION MIXTURES

The present invention relates to a process, which is improved with respect to the prior art, for working up reaction mixtures containing benzimidazolones prepared by reacting o-phenylenediamines and urea in a water-insoluble solvent.

Benzimidazolones may, as described in DE-A 27 25 957, be prepared by reacting an o-phenylenediamine with urea in an organic solvent at a temperature of 100 to 200° C. with elimination of ammonia. The solvent used is to have a boiling point of above 100° C. and to have a solubility in water of no more than 5 grams per 1 liter of water.

A disadvantage of this process is the technically complex work-up of the reaction mixtures produced. As can be taken from the examples of DE-A 27 25 957, the reaction mixture, which is a suspension of the benzimidazolone in the organic solvent, is filtered, the benzimidazolone filtered off is washed, firstly with ethanol or aqueous ethanol, and if appropriate with water, and dried in vacuo. This work-up is technically complex, since, on the one hand, a plurality of working steps are necessary and, on the other hand, the solvent used in the reaction and the aqueous ethanol arising in the work-up must be worked up in a complex manner. If washing with ethanol or aqueous ethanol and, if appropriate, water is omitted, the benzimidazolone must be freed from the solvent with a considerable expenditure of time and energy. Furthermore, because of the missing washing step, a benzimidazolone of a lower quality grade arises.

Departing from the teaching of DE-A 27 25 957, distilling off the solvent with water azeotropically could be contemplated. However, if it is attempted to remove the solvent with water azeotropically, even at the beginning of the distillation, vigorous foaming occurs, and at the end of the distillation the benzimidazolone begins to float on the water with considerable enlargement of the volume taken up. Both effects, foaming and floating, represent a considerable impairment and could only be overcome by a significant increase in the reactor volume. However, a procedure of this type would be accompanied by problems which would be scarcely capable of solution, since, on the one hand, appropriately oversized reactors are not conventionally available and, on the other hand, handling relatively small amounts of reaction mixtures in reactors which have very large volumes in comparison to the reaction mixture produced leads to technical difficulties.

There is therefore a requirement for a work-up process which avoids the abovementioned disadvantages and, in addition, can be implemented in a simple manner and without great technical complexity. In addition, the product of value is to be produced in high yield and simultaneously in high purity.

This object is achieved by a process for working up reaction mixtures containing benzimidazolones of the formula (I)

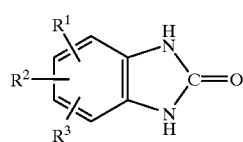

(I)

prepared by reacting o-phenylenediamines and urea in a water-insoluble solvent, where in formula (I) $R^1$, $R^2$ and $R^3$ are identical or different and independently of one another are a hydrogen atom, an alkyl, alkoxy or alkylsulfonyl group having in each case 1 to 6 carbon atoms, chlorine, bromine, a substituted or unsubstituted phenyl group, a carboxylic acid, methylcarbonyl, phenylcarbonyl, methoxycarbonyl, carbamoyl, methylcarbamoyl or phenylcarbamoyl group, a hydroxyl group, cyano group or nitro group. It comprises adding a wetting agent and a defoamer to the reaction mixture, distilling off the solvent azeotropically with the addition of water and with stirring and filtering off the benzimidazolone from the aqueous suspension arising.

Wetting agent is taken to mean surface-active compounds which decrease the surface tension of liquids, as a result of which the liquid spreads out better on surfaces and wets these.

Defoamers (antifoams) are surface-active substances which are sparingly soluble in the foaming liquid and, in film formation, displace the foam formers from the surface and by this means decrease or suppress the foam formation, or are substances which increase the surface tension of the water.

If only a wetting agent is added to the reaction mixture, although the floating of the benzimidazolone at the end of the distillation is prevented, at the same time the foaming is uncontrollably increased. If, on the other hand, only a defoamer is added, although the foaming at the beginning of and during the distillation is prevented, at the end of the azeotropic distillation, an agglutinated, unfilterable, expanded reaction mixture is obtained in which the benzimidazolone is present.

Only the simultaneous use of wetting agent and defoamer leads to the desired success and prevents the undesired foaming at the beginning of and during the distillation and the undesired floating of the benzimidazolone at the end of the distillation. This is surprising, since the properties of the wetting agent and of the defoamer are opposed to each other and one would expect that they would counteract each other in their effect. However, unexpectedly, this is not the case.

A further advantage of the process of the invention is that the solvent removed arises in a form of a purity such that it can be reused in the process without further work-up. The waste water also has only a low loading and thus does not represent a special problem.

A reaction mixture which contains a benzimidazolone of the formula (I), in which $R^1$, $R^2$ and $R^3$ are identical or different and independently of one another are a hydrogen atom, an alkyl group or alkoxy group having in each case 1 to 4 carbon atoms, chlorine, a hydroxyl group, cyano group or nitro group, in particular two of the radicals $R^1$, $R^2$ or $R^3$ are hydrogen atoms, can be used highly successfully in the process. The process is likewise suitable for using a reaction mixture which contains a benzimidazolone of the formula (I), in which $R^1$, $R^2$ and $R^3$ are hydrogen atoms, that is a reaction mixture which contains an unsubstituted benzimidazolone.

Conventional wetting agents can be used highly successfully in the process, for example an alkylsulfonate having 12 to 18 carbon atoms or a mixture of such alkylsulfonates, in particular a secondary linear alkylsulfonate having 12 to 18 carbon atoms or a mixture of such alkylsulfonates.

However, a paraffinsulfonate having 14 to 17 carbon atoms or a mixture of such paraffinsulfonates or alkylbenzenesulfonates having 10 to 13 carbon atoms or a mixture of such alkylbenzenesulfonates can be used as wetting agent.

Conventional defoamers may be used as defoamer. A trialkyl phosphate having 3 to 20 carbon atoms per alkyl radical or a mixture of such trialkyl phosphates, in particular tri-n-butyl phosphate may be used highly successfully as defoamer.

A defoamer containing a fat or oil, an ester of higher carboxylic acids, a higher alcohol, a polyalkylene glycol, polyglycol, silicone as surface-active substance or mixtures of the same, in particular a defoamer containing an ester of higher carboxylic acids, a higher alcohol, a polyalkylene glycol, polyglycol as surface-active substance or mixtures of the same can be likewise used as defoamer.

After the wetting agent and the defoamer have been added to the reaction mixture, the solvent is then distilled off with the addition of water. In the distillation, the water can be added to the reaction mixture in liquid form or in the form of steam. In a number of cases it can be expedient to distill off the solvent azeotropically with the addition of water in the form of steam. However, it is also possible to add the water to the reaction mixture in liquid form continuously or batchwise. However, water in liquid form and steam can also be used simultaneously.

Usually 0.1 to 5, in particular 0.25 to 2.5, preferably 0.4 to 1, % by weight of wetting agent is used, based on benzimidazolone.

Generally, it is sufficient to use 0.1 to 5, in particular 0.25 to 2.5, preferably 0.4 to 1, % by weight of defoamer, based on benzimidazolone.

If necessary, the wetting agent, just as the defoamer, can also be used in larger amounts, for example up to 10% by weight or more, based on benzimidazolone. However, in the majority of cases, the abovementioned amounts are sufficient, without any noticeable impairment of the process needing to be accepted.

Obviously, both the type of the benzimidazolone and also the type of wetting agent and defoamer used in each case can influence to a certain extent the amount of wetting agent and defoamer needed. This must be correspondingly taken account of if appropriate.

In the preparation of the benzimidazolone of the formula (I), an organic solvent which is insoluble in water, for example xylene, chlorobenzene, 1,2-dichlorobenzene, 1,3-dichlorobenzene, 1,4-dichlorobenzene, a mixture of isomeric dichlorobenzenes, 2-chlorotoluene, 3-chlorotoluene, 4-chlorotoluene, a mixture of isomeric chlorotoluenes, in particular 1,2-dichlorobenzene, 2-chlorotoluene or a mixture of isomeric chlorotoluenes is used as solvent.

In a number of cases it can be expedient to stir the reaction mixture using a radially acting agitator, in order to keep foaming low during the azeotropic distillation and, in this manner, to reinforce the effect of the wetting agent and of the defoamer.

The process of the invention may be carried out either at reduced pressure or at atmospheric pressure or superatmospheric pressure. It can be carried out either continuously or batchwise. It is particularly suitable for a batchwise procedure.

The water-wet benzimidazolone of the formula (I) arising after filtration can be further processed without additional work-up in a multiplicity of cases.

The examples below describe the invention in more detail without restricting it thereto:

Experimental Part

COMPARISON EXAMPLE 1

Azeotropic Distillation without Wetting Agent and without Defoamer

In a 3.0 l stirred flask equipped with water separator and reflux cooler, 273 g of phenylenediamine and 155 g of urea in 715 ml of 2-chlorotoluene are heated to 120 to 160° C. until the evolution of ammonia is completed. The mixture is then cooled to about 90° C. and the 2-chlorotoluene is carefully removed azeotropically with continuous addition of a total of 930 ml of water. The mixture is then cooled to room temperature, the solids are filtered off with suction and, after washing with a total of 1000 ml of water, 389 g of benzimidazolone having a water content of 15% are obtained. This corresponds to a yield of 99% of theory. Vigorous foaming occurs at the beginning of the azeotropic distillation, the volume of the reaction mixture increasing from initially about 1000 ml to about 1700 ml. In the final phase of the azeotropic distillation, the benzimidazolone begins to float, the volume of the reaction mixture increasing from 2500 to 3000 ml and the reaction mixture sometimes foaming up into the cooler.

COMPARISON EXAMPLE 2

Azeotropic Distillation with Wetting Agent, but without Defoamer

In a 3.0 l stirred flask equipped with water separator and reflux cooler, 273 g of phenylenediamine and 155 g of urea in 715 ml of 2-chlorotoluene are heated to 120 to 160° C. until the evolution of ammonia is completed. The mixture is then cooled to about 90° C. and 1.8 g of Hostapur SAS 60 (60% strength aqueous solution of secondary linear alkanesulfonates ($C_{12}$–$C_{18}$), a commercial product from Hoechst Aktiengesellschaft) are added. 2-Chlorotoluene is then removed with continuous addition of water. After removal of about 600 ml of 2-chlorotoluene and addition of about 780 ml of water, the mixture begins to foam uncontrollably. The experiment must therefore be terminated.

COMPARISON EXAMPLE 3

Azeotropic Distillation without Wetting Agent, but with Defoamer

In a 3.0 l stirred flask equipped with water separator and reflux cooler, 273 g of phenylenediamine and 155 g of urea in 715 ml of 2-chlorotoluene are heated to 120 to 160° C. until the evolution of ammonia is completed. The mixture is then cooled to about 90° C. and 1.8 g of tri-n-butyl phosphate are added. 2-Chlorotoluene is then removed with continuous addition of water. After removal of about 500 ml of 2-chlorotoluene and addition of approximately 650 ml of water, the reaction mixture begins to become more and more viscous, the volume of the mixture increasing from about 2000 to 2500 ml. The agglutinated benzimidazolone can only be rinsed out of the flask with a very large amount of water.

Example 1

Azeotropic Distillation with Wetting Agent and with Defoamer

In a 3.0 l stirred flask equipped with blade agitator, water separator and reflux cooler, 273 g of phenylenediamine and 155 g of urea in 715 ml of 2-chlorotoluene are heated to 120 to 160° C. until the evolution of ammonia is completed. The mixture is then cooled to <90° C., 1.8 g of Marlon A350 (mixture of alkylbenzenesulfonates ($C_{10}$–$C_{13}$), a commercial product from Hüls) and 1.8 g of defoamer FN (a fluorine-containing, nonsurfactant mixture of various polyalkylene glycol derivatives; a commercial product from Hoechst Aktiengesellschaft) are added and 2-chlorotoluene is then removed with continuous addition of in total 930 ml of water. The mixture is then cooled to room temperature, the solids are filtered off by suction and, after washing with a total of 1000 ml of water, 394 g of benzimidazolone having a water content of 16% are obtained, this corresponds to a yield of 99% of theory. During the azeotropic distillation, the volume of the reaction mixture increases from initially about 1000 ml to only 1300 to 1400 ml, only slight foaming being observable.

Example 2

Azeotropic Distillation with Wetting Agent and with Defoamer

In a 3.0 l stirred flask equipped with blade agitator, water separator and reflux cooler, 383 g of 4-nitro-1,2-phenylenediamine and 155 g of urea in 900 ml of 2-chlorotoluene are heated to 120 to 160° C. until the evolution of ammonia is completed. The mixture is then cooled to <90° C., 1.8 g of Hostapur SAS 60 (a 60% strength aqueous solution of a mixture of secondary linear alkanesulfonates ($C_{12}$–$C_{18}$), a commercial product from HOECHST Aktiengesellschaft) and 1.8 g of tri-n-butyl phosphate are added and 2-chlorotoluene is then removed with continuous addition of a total of 1100 ml of water, in which case the reaction volume increased by approximately 30 to 40%. The mixture is then cooled to room temperature, the solids are filtered off with suction and, after washing with a total of 1000 ml of water and drying in vacuo, 425 g of 4-nitro-2-benzimidazolone are obtained. This corresponds to a yield of 95% of theory.

Example 3

Azeotropic Distillation with Wetting Agent and with Defoamer

In a 3.0 l stirred flask equipped with blade agitator, water separator and reflux cooler, 273 g of phenylenediamine and 155 g of urea in 715 ml of 2-chlorotoluene are heated to 120 to 160° C. until the evolution of ammonia is completed. The mixture is then cooled to <90° C., 1.8 g of Marlon PS (a mixture of paraffinsulfonates ($C_{14}$–$C_{17}$), a commercial product from Hüls) and 1.8 g of defoamer FN are added, and 2-chlorotoluene is then removed with continuous addition of a total of 930 ml of water. The mixture is then cooled to room temperature, the solids are filtered off with suction and, after washing with a total of 1000 ml of water, 403 g of benzimidazolone having a water content of 18% are obtained. This corresponds to a yield of 99% of theory. During the azeotropic distillation, the volume of the reaction mixture increases from initially about 1000 ml to 1300 to 1400 ml, only slight foaming being observable.

Example 4

Azeotropic Distillation with Wetting Agent and with Defoamer

In a 3.0 l stirred flask equipped with blade agitator, water separator and reflux cooler, 273 g of phenylenediamine and 155 g of urea in 715 ml of 2-chlorotoluene are heated to 120 to 160° C. until the evolution of ammonia is completed. The mixture is then cooled to <90° C., 1.8 g of Hostapur SAS 60 (a 60% strength aqueous solution of a mixture of secondary linear alkanesulfonates ($C_{12}$–$C_{18}$)) and 1.8 g of defoamer (defoamer based on esters of high carboxylic acids; a commercial product of Hoechst Aktiengesellschaft) are added and 2-chlorotoluene is then removed with continuous addition of a total of 930 ml of water. The mixture is then cooled to room temperature, the solids are filtered off with suction and, after washing with a total of 1000 ml of water, 380 g of benzimidazolone having a water content of 13% are obtained. This corresponds to a yield of 99% of theory. During the azeotropic distillation the volume of the reaction mixture increases from initially about 1000 ml to 1300 to 1400 ml, only slight foaming being observable.

Example 5

Azeotropic Distillation, Additionally with Radially Acting Agitator

In a 30 l stirred flask equipped with a radially acting blade agitator, water separator and reflux cooler, 3630 g of o-phenylenediamine and 2064 g of urea in 10 l of 2-chlorotoluene are heated to 120 to 160° C. until the evolution of ammonia is completed. The mixture is then cooled to <90° C., 24 g of Hostapur SAS 60 (60% strength aqueous solution of secondary linear alkanesulfonates ($C_{12}$–$C_{18}$)) and 24 g of tri-n-butyl phosphate are added and 2-chlorotoluene is then removed with continuous addition of a total of 12 l of water. The mixture is then cooled to room temperature, the solids are filtered off with suction and, after washing with a total of 10 l of water, 5245 g of benzimidazolone having a water content of 15% are obtained. This corresponds to a yield of 99% of theory. During the azeotropic distillation, the volume of the reaction mixture increases from initially approximately 14 l to 18 to 19 l, only slight foaming being observable. Similar results are obtained with xylene or chlorobenzene as solvent.

What is claimed is:

1. A process for working up reaction mixtures containing benzimidazolones of the formula (I)

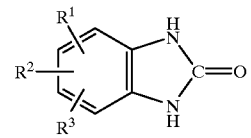

(I)

prepared by reacting an o-phenylenediamine and urea in a water-insoluble solvent, where in formula (I) $R^1$, $R^2$ and $R^3$ are identical or different and independently of one another are a hydrogen atom, an alkyl, alkoxy or alkylsulfonyl group having in each case 1 to 6 carbon atoms, chlorine, bromine, a substituted or unsubstituted phenyl group, a carboxylic acid, methylcarbonyl, phenylcarbonyl, methoxycarbonyl, carbamoyl, methylcarbamoyl or phenylcarbamoyl group, a hydroxyl group, cyano group or nitro group, which comprises adding a wetting agent and a defoamer to the reaction mixture, distilling off the solvent azeotropically with the addition of water and with stirring and filtering off the benzimidazolone from the resulting aqueous suspension containing the benzimidazolone.

2. The process as claimed in claim 1, wherein the reaction mixture contains a benzimidazolone of the formula (I), in which $R^1$, $R^2$ and $R^3$ are identical or different and independently of one another are a hydrogen atom, an alkyl group or alkoxy group having in each case 1 to 4 carbon atoms, chlorine, a hydroxyl group, cyano group or nitro group.

3. The process as claimed in claim 1, wherein the reaction mixture contains a benzimidazolone of the formula (I), in which two of the radicals $R^1$, $R^2$ or $R^3$ are hydrogen atoms.

4. The process as claimed in claim 1, wherein the reaction mixture contains a benzimidazolone of the formula (I), in which $R^1$, $R^2$ and R are hydrogen atoms.

5. The process as claimed in claim 1, wherein said wetting agent comprises at least one alkylsulfonate having 12 to 18 carbon atoms.

6. The process as claimed in claim 1, wherein said wetting agent comprises at least one secondary linear alkylsulfonate having 12 to 18 carbon atoms.

7. The process as claimed in claim 1, wherein said wetting agent comprises at least one paraffinsulfonate having 14 to 17 carbon atoms.

8. The process as claimed in claim 1, wherein said wetting agent comprises at least one alkylbenzenesulfonate having 10 to 13 carbon atoms.

9. The process as claimed in claim 1, wherein the defoamer comprises at least one trialkyl phosphate having 3 to 20 carbon atoms per alkyl radical.

10. The process as claimed in claim 1, wherein the defoamer comprises tri-n-butyl phosphate.

11. The process as claimed in claim 1, wherein a foam-reducing component of said defoamer is a fat or oil, an ester of higher carboxylic acids, a higher alcohol, a polyalkylene glycol, polyglycol, silicone as surface-active substance or mixtures of the same.

12. The process as claimed in claim 1, wherein a foam-reducing component of said defoamer is an ester of higher carboxylic acids, a higher alcohol, a polyalkylene glycol, polyglycol as surface-active substance or mixtures of the same.

13. The process as claimed in claim 1, wherein the amount of wetting agent which is added is 0.1 to 5% by weight, based on benzimidazolone.

14. The process as claimed in claim 1, wherein the amount of defoamer which is added is 0.1 to 5% by weight, based on benzimidazolone.

15. The process as claimed in claim 1, wherein, in said addition of water, the water is in the form of steam.

16. The process as claimed in claim 1, wherein the solvent is 1.2-dichlorobenzene, 2-chlorotoluene or a mixture of isomeric chlorotoluenes.

17. The process as claimed in claim 1, wherein said stirring step is carried out with a radially acting agitator.

18. The process as claimed in claim 1, wherein the solvent is recovered from the reaction mixture in a degree of purity sufficient for reuse in the process.

19. A process for separating a benzimidazolone from a reaction medium containing an organic solvent by azeotropic distillation in the presence of water, said solvent having a solubility in water of no more than 5 grams per liter of water; said benzimidazolone being a compound of the formula (I)

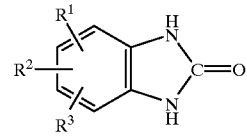

(I)

where $R^1$, $R^2$ and $R^3$ are identical or different and independently of one another are a hydrogen atom, an alkyl, alkoxy or alkylsulfonyl group having in each case 1 to 6 carbon atoms, chlorine, bromine, a substituted or unsubstituted phenyl group, a carboxylic acid, methylcarbonyl, phenylcarbonyl, methoxycarbonyl, carbamoyl, methylcarbamoyl or phenylcarbamoyl group, a hydroxyl group, cyano group or nitro group; said process comprising:

adding to said medium (1) an amount of defoaming, surface tension-increasing surface active agent which is sufficient to decrease foam formation during azeotropic distillation in the presence of water, and (2) an amount of surface tension-lowering wetting agent which is sufficient to inhibit, before the completion of the azeotropic distillation, floatation of the benzimidazolone on the resulting water-containing medium, distilling off said solvent azeoptropically, in the presence of water, and forming an aqueous suspension containing the benzimidazolone suspended in the resulting aqueous medium, and recovering the benzimidazolone from said aqueous suspension.

20. The process as claimed in claim 19, wherein said reaction medium is obtained by reacting an o-phenylenediamine and urea in said solvent, wherein the medium is stirred during the azeotropic distilling step, and wherein the benzimidazolone is recovered by filtering it off from said aqueous suspension.

* * * * *